US006573251B2

(12) United States Patent
Barritault et al.

(10) Patent No.: US 6,573,251 B2
(45) Date of Patent: Jun. 3, 2003

(54) DRUG AND PHARMACEUTICAL COMPOSITION FOR THE TREATMENT OF LESIONS OF THE NERVOUS SYSTEM AND FRACTIONS ENRICHED IN HEPARAN SULFATE

(76) Inventors: Denis Barritault, 4, rue Francaise, Paris (FR), 75001; Jean-Pierre Caruelle, 32, rue Jules Joffrin, Saint Maur (FR), 94100; Ahmed Aamiri, Block 22, N 7 Cite Hassan, Agadir (MA); Jean Gautron, 12, rue Antoine Bourdelle, Vitry sur Seine (FR), 94100

( * ) Notice: Subject to any disclaimer, the term of this patent is extended or adjusted under 35 U.S.C. 154(b) by 0 days.

(21) Appl. No.: 09/725,841

(22) Filed: Nov. 30, 2000

(65) Prior Publication Data

US 2001/0023246 A1 Sep. 20, 2001

Related U.S. Application Data

(63) Continuation-in-part of application No. 08/714,177, filed as application No. PCT/FR95/00401 on Mar. 29, 1995, now abandoned.

(30) Foreign Application Priority Data

Mar. 30, 1994 (FR) .............................................. 94 03805

(51) Int. Cl.$^7$ ............................................... A61K 31/715
(52) U.S. Cl. ............................................ 514/59; 514/54
(58) Field of Search ...................................... 514/54, 59

(56) References Cited

U.S. PATENT DOCUMENTS 5,605,891 A * 2/1997 Prino et al. .................... 514/54

OTHER PUBLICATIONS

Ball et al, Journal of Urology 148:211–215, 1992.*
Tardieu et al, J. Cell. Physiol. 150:194–203, 1992.*
Damon et al, J. Cell. Physiol. 135:293–300, 1988.*

* cited by examiner

*Primary Examiner*—Francisco Prats
(74) *Attorney, Agent, or Firm*—Jacobson Holman PLLC

(57) ABSTRACT

Use of at least one polymer or one biopolymer called HBGFPP, specifically protecting the growth factors of FGFs and beta TGFs families from tryptic degradation in the manufacture of a drug for the treatment of lesions of the nervous system.

4 Claims, 11 Drawing Sheets

D  CM  B  S

▲ FGF

○ FGF plus heparin

● FGF plus mesoglycan

△ FGF plus sulodexide

DAYS

○ FGF$_1$

● FGF$_1$ plus heparin

▲ FGF$_1$ plus mesoglycan

△ FGF$_1$ plus sulodexide

△ FGF$_2$

● FGF$_2$ plus heparin

▲ FGF$_2$ plus mesoglycan

○ FGF$_2$ plus sulodexide

FIG. 5 A

```
              1  2  3  4  5
66 000  —
21 000  —  ━    ━ ━ ━
14 000  —
           DALTONS
```

FIG. 5 B

```
              1  2  3  4  5
66 000  →
42 000  →
21 000  →    ●   ● ● ●
14 000  —   ━
           DALTONS
```

DRUG AND PHARMACEUTICAL COMPOSITION FOR THE TREATMENT OF LESIONS OF THE NERVOUS SYSTEM AND FRACTIONS ENRICHED IN HEPARAN SULFATE

RELATED APPLICATION

This is a continuation-in-part of application Ser. No. 08/714,177 filed Dec. 20, 1996, now abandoned as the National Phase of PCT/FR95/00401 filed Mar. 29, 1995.

This invention relates to the use of polymers or biopolymers for the preparation of a drug for the treatment of lesions of all origins affecting the central or peripheral system in human or veterinary medicine. It also concerns pharmaceutical compositions for this treatment. Lastly, it concerns fractions enriched in heparan sulfate.

The synthesis of CMDBS polymers (dextrans substituted by carboxymethyl, benzylamine and sulfonate) has been described in French Patent 2 461 724 and U.S. Pat. No. 4,740,594. Some of these polymers mimic heparin and may be used as plasma heparin replacement products, thanks to their anticoagulant and anticomplement properties.

Some of these CMDBS polymers mimic another property of heparin consisting of a stabilization, protection and potentialization of the in vitro biological activity of the growth factors of the FGF family (Tardieu and coll., Journal of Cellular Physiology, 1992, 150 pp. 194 to 203).

French patent 2 644.066 describes the use of certain CMDBSs associated with FGFs for healing the skin and the cornea. Experiments have been conducted by provoking a cutaneous wound with the help of a hollow punch 6 mm in diameter in the rat. In this example, the CMDBS associated with the FGF 2 makes it possible to obtain a clear effect on the speed and the quality of skin repair.

Another biopolymer, dektran sulfate, has also been advanced in association with FGFs as a stabilizer and protector, in Japanese Patent No. 13890. Dextran sulfate, moreover, is widely used in skin healing ointments and creams as well as in collyrium compositions, but, to the knowledge of the applicant, has no reported effect on the healing and regeneration of lesions of the nervous system.

A considerable number of factors whose activities facilitate the survival of nervous cells, the repair of central or peripheral nervous lesions, or muscular reinnervations have been described: polypeptide factors like Nerve Growth Factors (NGF), factors of the FGF families, brain derived factors like BDNFs, Ciliary Neurotrophic Factor (CNTF), Neurotrophin 3 (NT3), etc.

These factors have been used in experiments of muscular reinnervation, repairs of cuts of peripheral nerves, motor nerves, in models of lesions of cholinergic central nervous cells, and in numerous other models. For purposes of reference, the reviews listed below describe a part of this work: P. M. Richardson, Current Opinion in Neurobiology, 1991, 1: pp 401–406; T. Ebendal, Journal of Neurosciences Research, 1992, 32: pp. 461–470; P. G. Cordeiro, R. Brooke et al., Plastic and Reconstructive Surgery, 1989, 86 (3): pp. 1013–1019; Q. Yan, J. Elliott et al., Nature (Letters to Nature), 1992, 360: pp. 753–755; N. A. Seniuk, Journal of Reconstructive Microsurgery, 8 (5): pp. 399–404; F. Hefti P. P. Michel et al., Advances in Neurology, 1990, 53: pp. 123–127; A. C. Cuello, L. Garofalo et al., Progress in Brain Research, 1990, 84: pp. 301–311; A. Tadeka, H. Onodera et al., Brain Research, 1992, 569: pp. 177–180.

It thus emerges from an analysis of the state of the prior art that growth factors and polymers in association with growth factors have already been used in therapeutic applications.

However, none of the documents cited above shows that the polymers present effects by themselves, that is to say without being associated with growth factors.

Moreover, the activity of polymer-factor associations has been described only on certain lesions of a very specific type of tissue, namely the cutaneous tissue.

In view of the unpredictable nature of the therapeutic effects of a given molecule, it was not clear whether these polymers could have an effect on other tissues.

It is, in fact, well known that the different tissues of the human or animal body present structural and functional specific features making it impossible to predict the effect of a molecule, known for its effect on the cutaneous tissue or another tissue.

Similarly, it is well known that it is impossible to predict the in vivo activity of a molecule on a particular tissue from results obtained in vitro on a specific experimental model.

Surprisingly, it has been found, according to the invention, that certain polymers have a very marked effect on the speed of healing and of regeneration of tissue lesions of the central or peripheral nervous systems as well as on the quality of this healing and/or regeneration, in such a way that it may be measured by studying it using histological and physiological methods. Muscular reinnervation with reformation of a functional junction of the lesioned nerve with its muscle was observed.

This invention relates to the use of at least one polymer or one biopolymer, caller HBGFPP, with the exception of mesoglycan, specifically protecting the growth factors of the FGF and beta TGF families from tryptic degradation and not significantly inhibiting coagulation, in the manufacture of a drug for the treatment of muscular tissues.

In particular, such a polymer presents an anticoagulant activity of less than 50 international units per mg of polymer measured, according to Maillet et al. (Mol. Immunol, 1988, 25, 915–923). Preferentially, it does not substantially activate the complement system, that is to say, it possesses an anti-complement system of above 0.5 $\mu$g for the $CH_{50}$ (according to Mauzac et al., Biomaterials, 6, 61–63, 1985).

Advantageously, the polymer potentializes the FGFs in vitro.

According to the invention, polymers are understood to mean any natural substance, chemically modified natural substance or totally synthetic substance responding to the definition given above.

The following polymers are therefore concerned:
polymers obtained from dextrans but modified by other types of substitutions with other types of radicals,
natural polymers other than those deriving from dextrans but including osidic residues (cellulose, chitin, fucans, etc.),
polymers obtained by polymerization of monomers of non-osidic nature (modified or unmodified malic polyacid, oxalic polyacid, lactic polyacid, polystyrene, polyethylene glycol).

Advantageously, the said polymer or biopolymer is a polysaccharide which may be primarily composed of glucose residues.

Such a polysaccharide advantageously presents a molecular weight above 10 kD and advantageously about 40 kD.

It may also comprise glucosamine and/or uronic acid residues, particularly in the form of glucosamine dimer-uronic acid.

Particularly preferred polysaccharides are substituted dextrans, glycosaminoglycans possibly in association with a lipid, a peptide or a protide, or sulfates of these polymers.

This invention also relates to a pharmaceutical composition containing these polymers.

The polymers and/or biopolymers may be selected from natural substances which may then be modified, if required, by additions of appropriate chemical groups, or again be obtained entirely by synthesis. These natural, semi- or wholly synthetic polymers are then selected on the basis of their ability to interact specifically with several growth factors, notably those of the FGF and the beta TGF families. They are also selected on their ability to protect this (or these) factor(s) against proteolytic degradations. These polymers will be referred to under the generic abbreviation HBGFPP (heparin binding growth factor protectors and promoters).

Two prototypes of these polymers or biopolymers are given as examples together with the processes and selection criteria of these polymers.

The first HBGFPP example belongs to the CMDBS family which are known products, namely functionalized biospecific dextrans, substituted by carboxymethyl, benzylamide and benzylamine sulfonate. These polymers illustrate the yielding of HBGFPPs from natural products (dextrans) which are subsequently chemically substituted.

The second example describes the selection of wholly natural products such as purified sulfate proteoglycosaminoglycans from tissular extracts.

These two examples illustrate the ability of these HBGFPPs to interact, stabilize, protect and potentialize the growth factors of the FGF and beta TGF families, and their use in a pharmaceutical composition permitting a healing and a regeneration of nervous liaisons and a protection and healing of the nervous cells.

In this patent application, by <<treatment>> is meant any curative or preventive operation carried out for the prophylaxis, the healing, the protection or the regeneration of lesions touching the nervous system.

Thanks to the action of the HBGFPPs and in particular the CMDBSs, as the examples below illustrate, the reinnervation of the EDL or Soleus type muscle is accelerated. This reinnervation is manifested by the regeneration of the nervous fiber and the speedy reformation of a functional synaptic junction.

Not only is there an increase of axonal growth in lesions near the muscle but also a control of this growth. Thus, with respect to sprouting, this growth takes place in an organized and directed way resulting in an acceleration of functional repair.

The properties of HBGFPPs are such as to make this family of molecules a totally new and unique class of drugs which may be used to favor and improve lesions of the central or peripheral nervous system, directly touching the neuronal cells and their axonal and dendritic prolongations, cholinergic or dopaminergic neurons or again touching cells associated with neurons such as oligodendrocyte astrocyte glia cells and Schwann cells. These lesions may be of any origin: traumatic, iatrogenic or chemical, due to the use of radiation or induced by surgical operations, of bacterial, parasitic or viral infectious origins, of auto-immune origin, or lesions and deteriorations may be induced by bleedings such as ruptured vessels. These new drugs are also used in the treatment of neurodegenerative diseases such as Parkinson's or Alzheimer's disease, or of genetic origin. Lastly, these drugs may with benefit be associated with cells used in treatments of transplantations in the affected areas of the brain, using normal or genetically modified cells.

The drug and the pharmaceutical composition according to the invention may contain an effective quantity of HBGFPP, for example CMDBS associated with one or more compatible and pharmaceutically acceptable vehicles. It may also be associated with pharmaceutical agents such as anti-inflammatory agents and/or antibacterials.

The vehicle may be physiological serum or buffers such as PBS containing 0.15M NaCl or any other compatible solution which does not irritate the damaged nervous tissues. Formulations providing thick or gel solutions according to standard techniques known to the person of ordinary skill in the art may be proposed depending on the type and the accessibility of the lesion.

Advantageously, such a composition is designed to be injectable directly on the site of the lesion at a dose of 2.5 to 2500 mg/ml of HBGFPP as exemplified by CMDBS, or like natural HBGFPP biopolymers such as mesoglycan, but the intravenous or intramuscular route may be preferred in the case of de-innervation of de-innervated muscle. Injection in the spinal cord may also be preferable in the case of lesions of said spinal cord or of lesions of branches of prolongations of nervous fibers being motor and/or sensitive fibers. The injection volume is estimated in function of the size of the lesion. Doses corresponding to 100 $\mu$l often prove sufficient.

In addition to the "Heparin Binding" growth factor protection qualities, the HBGFPPs selected according to the tests described below present a very low anticoagulant activity compared to that of heparin, too weak to hamper coagulation in the case of a trauma. In the case of an injection by intravenous route, the injected dose must be adjusted to the blood volume of the man or animal treated in this way so that the dose of HBGFPP in the blood also lies between 2.5 and 2,500 mg/ml.

In the examples described in the following pages, concerning the reinnervation of the skeletal muscle of the male EDL-type rat (Extensor Digitorum Longus) or the postural slow muscles (soleus), a single injection of 100 $\mu$l of a solution of CMDBS at 50 $\mu$g/ml on the site of the wound induces a complete reinnervation in 17 days, whereas, in the case of the EDL muscle, this innervation is observed only after 60 days when no treatment is given. With regard to the soleus muscles, the CMDBS effect is even more pronounced since, after injection of CMDBS, reinnervation is total and functional in 17 days whereas the reinnervation of the controlateral muscle is defective even after 60 days. These effects are specific to the HBGFPPs and notably certain CMDBSs responding to selection criteria with respect to FGFs and beta TGF family growth factor protection against proteolytic degradations induced by the action of trypsin. This specificity may be illustrated by comparing the effects of repairing nervous tissue lesions by HBGFPPs and related products such as heparin, dextran, dextran sulfate or sucrase (sucrose octyl sulfate). Although these molecules interact with the FGFs, and at any rate as far as heparin is concerned with beta TGF, neither sucrase, nor heparin nor dextran sulfate protect the beta TGF against the proteolysis induced by the action of trypsin, as is shown by the application of screening and selection tests of the HBGFPPs described in the examples below. These products have no effect on lesions of the nervous tissues. Thus, by carrying out in vitro screening on the basis of a double protection of the FGFs and beta TGFs against the proteolysis induced by Trypsin, it is possible to select HBGFPPs, like certain CMDBSs including those given in these examples. These same selection criteria applied to natural biopolymers such as mesoglycan or sulodexide have shown that mesoglycan, which presents a double protection and stabilization activity for both FGFs and beta TGFs, has a beneficial activity in nervous repair and regeneration, and, as such, belongs to the HBGFPP family, whereas sulodexide, which protects the FGFs against the proteolysis induced by the activity of trypsin, has no significant protective action against the action of trypsin on beta TGFs.

This invention also relates to fractions of mesoglycan or sulodexide enriched in heparan sulfate, presenting advantageously 80%, and preferably 95%, of heparan sulfate.

Such fractions may be obtained by a heparan sulfate enrichment process of a glycosaminoglycan composition, comprising the following stages:

ion exchange chromatography of the composition, elution on a DEAE gel, treatment by ABC chondroitinase, chromatography on molecular sieve, and heparan sulfate elution.

BRIEF DESCRIPTION OF THE DRAWINGS

The invention will be illustrated, but in no way limited by, the following examples in which:

FIG. 5A illustrates the protective effect of heparin, mesoglycan and sulodexide against a proteolytic degradation of the $^{125}$I-FGF1. Proteolytic digestion was carried out at 37° C. and the samples were separated by 18% polyacrylamide gel electrophoresis. The gels are dried and autoradiographed. The first track contains the $^{125}$I-FGF1 on its own. The $^{125}$I-FGF1 is incubated in the presence of trypsin (lame 2), heparin (lame 3), mesoglycan (lame 4) or sulodexide (track 5).

FIG. 5B illustrates the protective effect of heparin, mesoglycan and sulodexide against a proteolytic degradation of the $^{125}$I -FGF2. The arrangement of the lames is identical to that presented for the $^{125}$I -FGF1 in FIG. 5a.

FIG. 7A represents a section of adult normal EDL muscle. The motor plaques of the fast fibers have a highly developed and differentiated synaptic groove (top left) (×150).

FIG. 7B represents an EDL muscle section after 60 days of regeneration without treatment. The plaques have reformed well, with a diameter analogous to that of the equivalent control but the surface and the synaptic differentiation are weaker (×150).

FIG. 7C represents an EDL muscle section after 17 days of regeneration, treated by CMDBS. The diameter of the plaque is comparable to the previous ones but the surface and the synaptic differentiation are considerably higher (×450).

FIG. 7D represents a section of adult normal Soleus muscle. The diameter of the plaque is identical to that of the EDL muscle but the differentiation of the groove is less high (×300).

FIG. 7E represents a section of Soleus muscle after 60 days of regeneration without treatment. The AChE indicates the position of the plaques which have a diffuse aspect, without visible groove and smoothed out. The motor axons are not visible. These observations are in favor of a non reinnervation (×150).

FIG. 7F represents a Soleus muscle section after 17 days of regeneration, treated by CMDBS. The synaptic groove is clearly differentiated and is distinctly marked by the AChE. The axons are visible at the motor plaque level (×300).

EXAMPLE 1

CMDBS Preparation and Selection a) CMDBS Preparation

CMDBSs are dextrans substituted by carboxymethyl, benzylamide and benzylamide sulfonate groups. The method of synthesizing the CMDBSs may be that described by M. Mauzac and J. Josefonvicz in Biomaterials 1984, 5, pp. 301–304. According to this process, carboxymethyl dextran (CMD) is prepared from dextran by substituting several glycosylated units with carboxyl groups on the carbon in positions 5 and 6. In the next step, benzylamide is coupled with the carboxyl groups to form carboxymethyl-benzylamide dextran (or CMBD). Lastly, a few aromatic nodes of benzylamide are sulfonated in order to yield carboxymethyl dextran benzylamide sulfonate or CMDBS.

The sodium salts of these derivatives are ultrafiltered, lyophilized and dissolved in the appropriate buffer prior to use.

Figure 1:
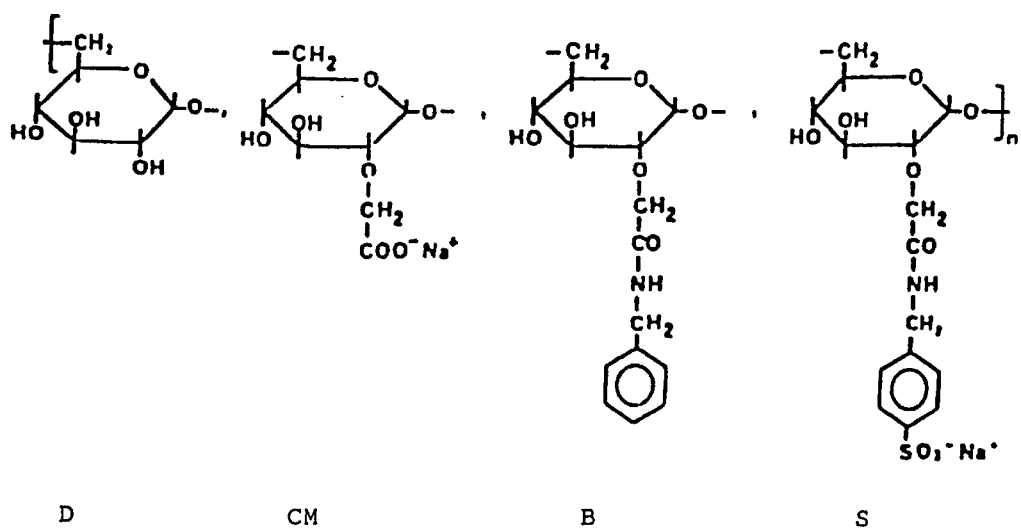
FIG. 1 represents the CMDBS formula.

The general formula of the CMDBSs is illustrated in FIG. 1.

The CMDBSs possess a statistical distribution of the different substituents. The percentages for each CMDBS type are determined using standard methods.

b) CMDBS Selection i: FGF Protection and Stabilization Tests

During the synthesis of the CMDBS the substitution rate of each of the groups may be controlled by modifying the substitution reaction conditions. Control of such parameters as temperature, reaction time, relative concentrations of the constituents, substitution reaction number, etc., makes it possible to obtain a very large number of substituted polymers. The substitution of the hydroxyls by carboxymethyl on the carbons in positions 5 and 6 gives carboxymethylation rates ranging from 0 to 200% (100% for each of the carbons in position 5 and 6). The carboxymethyl group may be, in turn, partially or totally used for fixing the benzylamide. The benzylamide groups may be partially or totally used for the sulfonation. The functionalized substituted dextrans used according to the invention are among those specifically described in French Patent 2.461.724. In addition to its ability to stabilize and protect FGF family growth factors, as described in the publication of Tardieu et coll., J. Cell. Physio. 1992, 150, pp 194 to 203 and in French Patent 2.461.724, the selected CMDBS must be able to interact with at least one member of the beta TGF family of growth factors according to an evaluation method described below, and to protect the beta TGFs against proteolysis.

ii. Evaluation of the Interaction Capacities Between CMDBS and Beta TGF Family Growth Factors.

In order to measure the capacity of certain CMDBSs to interact with members of the beta TGF family and, by means of this interaction, to protect the beta TGFs, a screening test was designed. This test consists in measuring the ability of the selected CMDBS to allow the beta TGF to maintain its biological activity despite a protease treatment.

In the example below, the CMDBS used is batch 26.2 defined by a substitution rate of 110% of carboxymethyl units, 3.6% of benzylamide units and 36.5% of sulfonate units, and possesses an anticoagulant activity of 4 IU/mg (International Units). This batch's anti-complement activity is 1.1 $\mu$g of $CH_{50}$ measured according to Mauzac et al. (previously cited).

The heparin used as control was supplied by the Sanofi company (Choay Institute) and presents an anticoagulant activity of 175 IU/mg.

The beta 1 TFG is prepared from human blood platelets according to a protocol described in numerous publications (for example Growth factors and their receptors, 1992, vol 1 pp 419–472, written by A. Roberts and M. Sporn, edited by A. Roberts and M. Sporn, and published by Springer Verlag Berlin) and are commonly used by persons of ordinary skill in the art. The beta TGF biological activity test used in this example is that of the inhibition of CCL64 cells (from the American Tissue Culture Collection). This inhibition is measured by the ability of the beta TGF to inhibit the incorporation of tritiated thymidine in a dose dependent manner in these CCL64 cells stimulated by the FGF or by fetal calf serum according to the protocol described by Van Zolen in Progress in Growth Factor Research, 1990, 2, pp 131 to 152.

The beta TGF is used in two doses, one corresponding to the 50% inhibition capacity of the incorporation of tritiated thymidine (defined as the inhibiting activity unit) and the other corresponding to the 100% inhibition capacity. In this example, the values obtained are 250 pg of TGF for the CCL64 cells cultivated in 1 ml of culture medium.

A 50 ng sample of beta TGF in saline phosphate buffer containing 0.1% of bovine albumin serum (from the SIGMA company, Saint Louis USA) is incubated on its own, or associated either with 5000 $\mu$g of CMDBS or 5000 $\mu$g of heparin, with or without 500 $\mu$g of trypsin. The final volume of the incubated solution is adjusted to 1 ml and incubation is carried out at 37° C. for a varying length of time (10 minutes in the example described (Table 1)).

20 $\mu$l samples of a volume of are taken from each of the incubation reactions and added to CCL64 cells cultivated in 24-well plates, each well containing one milliliter of culture medium according to the aforementioned protocol described by E. Zohlen. In these conditions, the final concentration of beta TGF per well is 1 ng/ml. Table 1 summarizes the results obtained in various conditions and shows the protective effect of the CMDBS. Thus, after 10 min of incubation at 37° C., 75% of the biological activity of the beta TGF is still present, whereas heparin, despite the fact that it can be fixed to the beta TGF (Mac Caffrey et al., J of Cell. Physiology, 1992, vol 52, pp 430–440), does not protect the beta TGF against this proteolytic degradation (less than 20% of biological activity remains). It should be remembered that, in the case of FGFs, heparin provides protection against proteolysis induced by trypsin (Tardieu et al., Journal of Cellular Physiology, 1992, 150: pp 194–203).

It was verified that the CMDBS had no inhibiting power on the activity of trypsin (Table 2). Thus, 10 $\mu$g of trypsin were incubated, either with a substrate (S.87 supplied by the Serbio company in Paris and used according to the supplier's recommendations) or with this substrate and a trypsin inhibitor such as that originating from soya (such as the soybean trypsin inhibitor or STI from Sigma), these incubations being carried out in the absence or presence of varying quantities of CMDBS (batch AM26). The enzymatic activity of trypsin was measured by spectrophotometric absorption of the transformation product of S 87 versus the incubation time.

EXAMPLE 2

Selection of Other HBGFPPs

Two commercial preparations of proteoglycosaminoglycan and glycosaminoglycans were selected according to their ability to interact with the growth factors of the FGF and beta TGF families.

Preparations of heparan sulfate obtained by fractionating mesoglycan and sulodexide were also tested.

The mesoglycan and sulodexide were supplied by the previously mentioned Sigma Chemical Co, Saint Louis Mo. USA.

Figure 2:
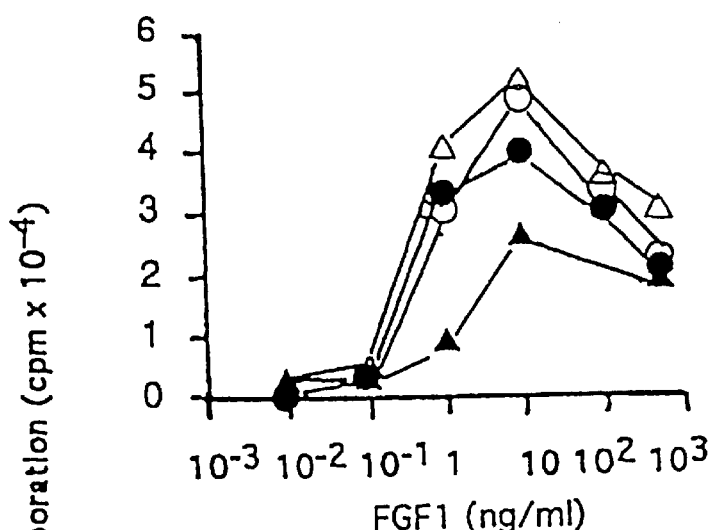
FIGS. 2A and 2B illustrate the potentialization of the biological activity of FGF1 (2a) and FGF2 (2b) by heparin, mesoglycan and sulodexide. Biological activity is measured on CCL39 cells by measuring the increased incorporation of tritiated thymidine in function of the dose of FGF1 and FGF2 added alone or in the presence of 20 μg of heparin, 10 μg of mesoglycan or 10 μg of sulodexide.
Figure 2:
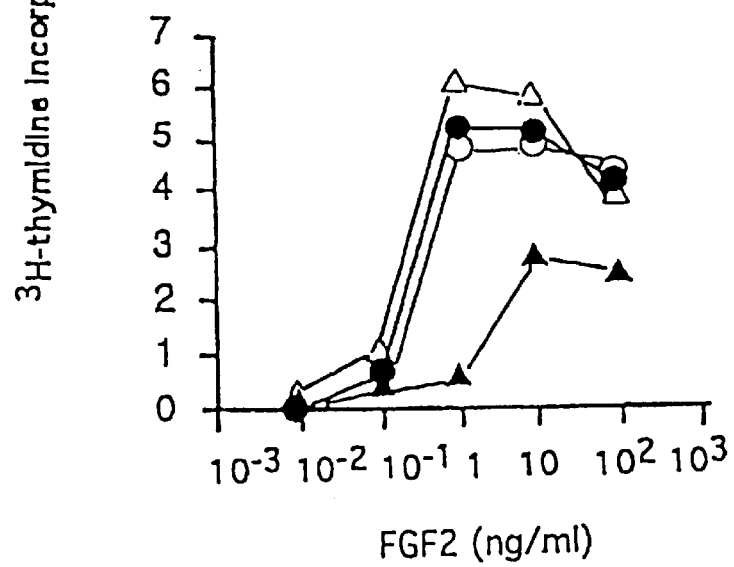
Figure 3:
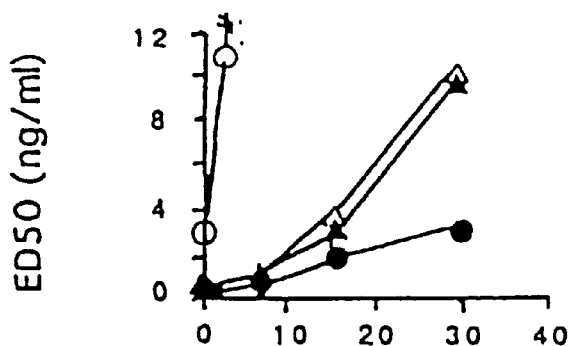
FIGS. 3A, 3B, 4A and 4B illustrate the protective effect of heparin, mesoglycan and sulodexide against a thermal degradation of FGF1(3), and FGF2(4). FGF samples are incubated on their own or in the presence of 20 μg of heparin, 10 μg of mesoglycan or 10 μg of sulodexide at 20° C. (a) and 37° C. (b) for 1, 7, 15, 30 days. The measurement of the biological activity presented in abscissa corresponds to the stimulation unit values ($ED_{50}$) of the incorporation of tritiated thymidine in CCL39 cells.
Figure 3:
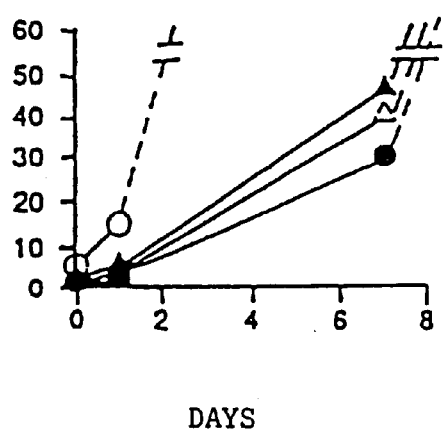
Figure 4:
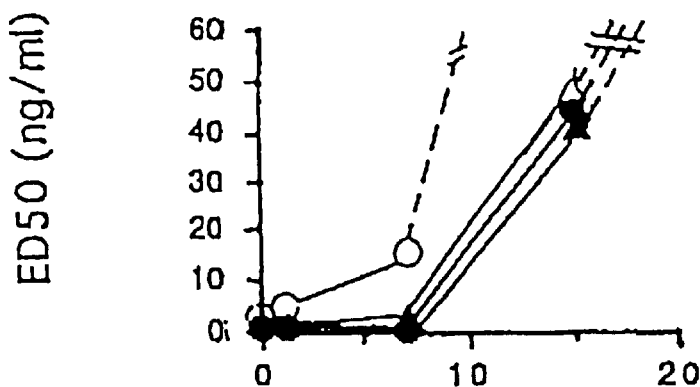
Figure 4:
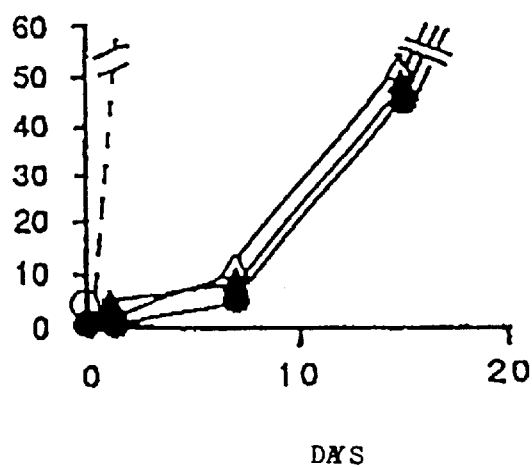

The cells used in this example are CCL39 cells from the American Tissue Culture Collection. The conditions concerning culture and the measurement test of FGF biological activity are the same as those described in the publication by Tardieu and coll. in the Journal of Cellular Physiology, 1992. Their properties are summarized in Table 3. The FGF growth factors used are the FGF 1 and FGF 2 recombinant forms.

a) Effect of Mesoglycan and Sulodexide on the Biological Activity of the FGFs in Vitro In these experiments, the FGF 1 or 2 is used at a dose corresponding to the effective dose (called $ED_{50}$) in order to induce a stimulation of the biological activity of 50% of the dose inducing the maximum stimulation. The biological activity is measured by the ability to induce an increase of the incorporation of tritiated thymidine in the cells according to protocols extensively described in numerous publications such as the previously mentioned publication by Tardieu et coll., and also in French Patent 2 644 066. In this example, the $ED_{50}$ is 5 ng/ml for the FGF 1 and 3 ng/ml for the FGF 2, these values being experimentally measured (FIGS. 2A and 2B). The same stimulation experiment in function of the FGF dose is carried out in the presence of 10 $\mu$g/ml of mesoglycan or sulodexide, or 20 $\mu$g/ml of heparin. FIG. 2 shows that in these conditions the $ED_{50}$ becomes 0.4 ng/ml and 0.2 ng/ml respectively for FGF 1 and FGF 2 in the presence of these doses of sulodexide or heparin. In addition to this ability to potentialize the biological activity of the FGFs, the HBGFPPs protect the FGFs against thermal degradations and the inactivation induced by the proteolytic action of trypsin (FIGS. 3 and 5). Similarly, these HBGFPPs protect FGF1 and 2 against an inactivation induced by the proteolytic activity of trypsin (FIGS. 5A and 5B).

b) Protective Effects of Mesoglycans, Sulodexides, Dextran, Dextran Sulfate and Sucrase with Regard to Beta TGFs.

Several other compounds were evaluated: dextran sulfate (Sigma Chemical, molecular weight 40.000, the dextran having been used for the synthesis of the CMDBS (also from Sigma)), sucrase or sucrose octasulfate (supplied by D. Bar Shalom, Bukh Medic company, Denmark). Some of these compounds were chosen because they protect and stabilize FGFs, for example sucrase (see. U.S. Pat. No. 5,202,311) or dextran sulfate (see. Japanese Patent 138 907/88). The dextran is the one used in the synthesis of CMDBS AM26.

The protection experiment of the beta TGF biological activity was carried out in the same way as with the CMDBS as described in Example 1 ii. The incubation mixture contained 50 ng of beta TGF (in 0.1% bovine serum albumin) and trypsin (500 µg). Mesoglycan or sulodexide or dextran sulfate or dextran or sucrase are used at the dose of 5000 µg.

The beta TGF biological activity is measured as described above after a dilution of 50 times and by using CCL64 cells.

The results are presented in Table 4.

These results show that, with the exception of certain CMDBSs capable of responding to the two selection criteria with regard to the FGFs and beta TGFs, only mesoglycan, among the other compounds tested, presents a significant protective activity for the beta TGFs.

c) Isolation of the Heparan Sulfate Fraction of Sulodexide and Mesoglycan

Sulodexide and mesoglycan correspond to mixtures of several substances essentially made up of different glycosaminoglycans (GAG).

By means of a first purification stage, it was established that a gram of dry product of each of these two products contained respectively 874 mg for the mesoglycan and 795 mg for the sulodexide of total GAGs.

This purification was obtained by subjecting these solubilized products to ion exchange chromatography (DEAE-Trisacryl) in order to remove all proteic contaminants. The total GAGs were then purified by eluting the DEAE gel with a sodium acetate solution, pH 4, containing 1.5 M NaCl.

After an extensive dialysis phase against water, 60 mg of each product of GAG are digested by the ABC chondroitinase overnight at 37° C. (1 unit per mg of GAG). This enzyme degrades all the GAGs with the exception of the heparan sulfates (HS). The products of digestion were subjected to molecular sieve chromatography (G50 Sephadex, 1.8×95 cm column). Elution is then carried out on ammonium bicarbonate buffer at a rate of 18 ml/hour. The non digested material corresponding to HS-type GAGs is collected in the elution dead volume of the column.

The GAG concentrations are calculated from their uronic acid content using the carbazol method (Bitter T. and Muir H. M., 1962, Anal. Biochem 4, pp 330–334).

From these measurements the following composition of each of the products was obtained:

Sulodexide Mesoglycan

|  | Sulodexide | Mesoglycan |
| --- | --- | --- |
| Total GAGs | 79% | 87% |
| Heparan Sulfate Fraction (HS) | 48% | 52% |
| Other GAGs | 31% | 35% |

Figures 6A, 6B:
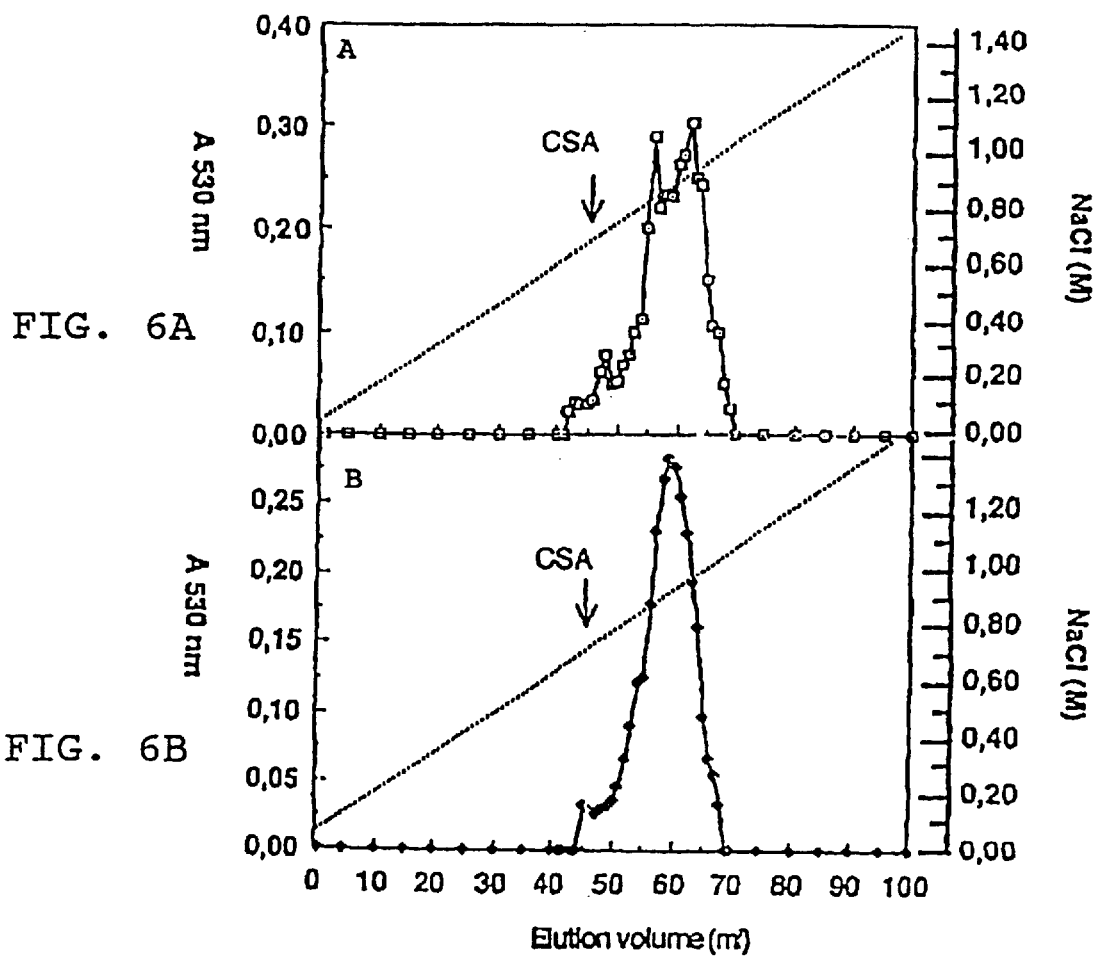
FIGS. 6A and 6B are DEAE-Trisacryl column elution profiles, respectively of HSM fractions (FIG. 6A) and HSS fractions (FIG. 6B) in the presence of chondroitin sulfate (CSA) fractions for the calibration of the column.

The HS fractions of each of these two products were again chromatographed on a DEAE Trisacryl gel. 1 mg of each HS fraction, purified with mesoglycan (FIG. 6A) or sulodexide (FIG. 6B) in 3 ml, was deposited on a balanced column with 0.05 M NaCl buffer, 0.05 M TMS-Hcl pH 7.5. After washing of the column with 10 volumes of the same buffer followed by washing with 10 volumes of 0.05 M NaCl buffer, 0.05 M of sodium acetate pH 4, the material fixed to the column is desorbed by a saline gradient ranging from 0.05 M NaCl to 1.5 M NaCl in the same acetate buffer. 1 ml of each fraction collected was measured by the carbazole method.

The material corresponding to the HS constituents of each of the original products shows approximately the same elution profile and thus roughly the same apparent load. This elution peak maximum is obtained for a saline concentration of 0.94M NaCl. A defined fraction of chondroitine sulfate (CSA) was subjected to the same protocol in order to calibrate chromatography. This CSA fraction, containing only one sulfate group by disaccharide, is eluted at the ionic strength of 0.72 M NaCl.

These results show that the HS fraction contains more sulfate groups than the reference CSAs. The HS fraction presents about two sulfate groups per dissacharidic unit.

These fractions were tested in order to discover their protective power with regard to the beta TGF and the FGF compared to the powers established with the respective raw products.

Semi-quantitative Evaluation of the Protective Effects of the FGF by Different Polymers As described above, a constant quantity of radioactive FGF is incubated under different conditions. After autoradiography of the reaction products, the non degraded quantity of radioactive FGF is quantified by densitometry. The values corresponding to the percentage of radio-labelled FGF found compared to the quantity deposited at the start of reaction (Table 5).

The results of Tables 4 and 5 show that the HSM and HSS fractions, originating respectively from mesoglycan and sulodexide, present protective effects which are greater than these two compositions and are close to 100%.

EXAMPLE 3

In Vitro Inhibiting Effects of CMDBSs and Glycosaminoglycans on the Activity of Leukocytic Elastase and Plasmin The inhibiting powers of different CMDBS and the intermediate compounds of their synthesis were established for leukocytic elastase and plasmin.

The purified leukocytic elastase was obtained by Elastin Products Co (Owenville, Mo., USA) and the plasmin from SIGMA.

The inhibition of enzymatic activities by these different compounds is carried out at 37° C. in a thermostatic bath. The enzymes under consideration are placed in solution in a 100 mM Tris-HCL buffer, pH 8 for the elastase and pH 7.4 for the plasmin, in the presence of 0.02% sodium azide and 0.01% Triton X100 for the plasmin. The substrate and enzyme concentrations are: 0.10 mM MeO-Suc-Ala-Ala-Pro-Val-pNA (paranitroanilide) for the elastase at 8.3 nM, and 0.20 mM dVal-Leu-dLys-pNA for the plasmin at 77 nM. The $IC_{50}$ is determined for each of the conditions.

Table 6 gives the results obtained, in which batch AM6 corresponds to a T40 dextran of 40,000 kD. Batch EM5 corresponds to a T10 dextran of 10,000 kD. The intermediate products of synthesis are identified by the symbols given above with an index number specifying the number of each substitution reaction.

The $IC_{50}$ values show that the CMDBSs have non competitive hyperbolic-type inhibiting effects on leukocytic elastase activity which are comparable to those of heparin, one of the best inhibitors of this activity (Ki of the order of 1 nM). In addition, and unlike heparin, the CMDBSs has inhibiting effects on plasmin.

Table 6 also shows that the inhibiting effects of the HSM and HSS fractions are greater than those of mesoglycan and sulodexide respectively.

EXAMPLE 4
Effect of CMDBS on the Reinnervation of the Skeletal Muscle of the Adult Rat in the Course of Post-traumatic Regeneration
INTRODUCTION Previous work (Schultz E. Anat, Rec. 1984, 208, pp. 501–506; Bassaglia Y. Thesis of Paris University-XII, Créteil, 1991) has shown that the postural slow muscles in regeneration (Soleus type) presents a motor reinnervation de fault in relation with alterations of the muscular basal blades. These basal blades play the role of a functional interface at synapse level. The motor axons of these muscles are unable to find their former targets and the non reinnervated muscular fibers undergo a fibrotic degenerescence two months after the lesion.

This post-trauma involutional phenomenon does not occur in rapid phasic muscles of the EDL type (Extensor digitorum longus) whose fibers recover their functionality at the end of two months.

An analogue of matricial heparan synthesis, CMDBS (carboxymethyldextrane benzylamide sulfonate) was found to be particularly effective in increasing the speed and the degree of regeneration of the two types of muscles, particularly the Soleus muscle. The CMDBS was used in an experiment on the reformation of the motor plaques of regenerating muscles, treated or not by CMDBS, over a time interval of 1 to 60 days.

The histological study of the reinnervation was carried out by revealing cytochemically the acetyl choline esterase (AChE), (Gautron J. Histochem., 1982, 76, 469–478), of the motor plaques combined with a method of argentic impregnation of the axons (Hopkins W. G., J. Physiol. 1981, 320, 5–6) in sections of muscles.

Among the principal isoforms of AChE (4S, 10S and 16S), the dodecameric asymmetric form 16S is concentrated at the neuromuscular synapse in the rat. It connects by ionic interaction to the basal by means of a triple helix of collagen (Vigny M., Koenig J. and Rieger F. J., Neurochem., 1976, 27, 1347–1353; Blondet B. and Gautron J., J. Biol. Cell., 1980, 38, 203–210; Blondet B., Rieger F., Gautron J. and Pinton-Raymond M., Dev. Biol. 1986, 117, 13–23). This isoform constitutes a sensitive biochemical indicaation of very fine molelcular modifications of the synaptic basal blades.

The degree of reinnervation of the regenerated muscles was measured by assaying the choline acetyl transferase. This synthesis enzyme of the chemical mediator in the terminal buttons constitutes a specific label of axonal growth inside the muscle. A rise in its activity notably accompanies the sprouting of the axons.

MATERIAL AND METHODS
1—Lesion of Skeletal Muscles 45 male Wistar rats, aged two months and a half and divided into two batches treated in parallel for histological studies on sections or biochemical studies after homogenization, were used for the experiment.

The rats were anesthetized with ether. The EDL and Soleus muscles were lesioned by crushing by means of a Péan forceps with pressure maintained for about 10 seconds in order to damage the fibers in the middle of the muscle. Prior to this, the motor nerves had been cut, at the entrance of the muscle, so as to avoid an irreproducible lesion of the axons during crushing of the muscle. 100 $\mu$l of CMDBS at 50 $\mu$g/ml, heated at 37° C., was injected in 20 seconds in the muscle, using a Hamilton microsyringe fitted with a needle 50 mm in length and 0.3 mm in diameter. The untreated contralateral muscles were used as controls so as to cancel out individual variations.

The rats woke up 10 minutes after anesthesia. They recovered motor activity in 30 minutes. The operated rats were placed in separate 6 $dm^2$ cages and fed at will.

2—AChE Cytochemistry

The enzyme was revealed by the J. Gautron method (Hopkins W. G., J. Physiol., 1961, 320, 5–6). The muscles fixed by the 4% formaldehyde were cut longitudinally at a thickness of 80 mm using a freezing microtome. After rinsing, the sections were incubated for 30 minutes in the developing medium containing 50 ml of acetyl sulfur (Aldrich ref.: A2, 220–3), 1 ml of 3% $Pb(NO_3)$ in water, 50 mg of acetylthiocholine bromide (Aldrich ref. 85, 533–2) in 100 ml of 0,2M Tris-maleate-NaOH buffer, pH 6.8.

3—Argentic Impregnation of Axons

After development of ACE, the longitudinal sections are dehydrated by 100% ethanol, then rehydrated in distilled water and incubated for 30 minutes in the argentic solution containing 0.31 g of boric acid, 19 mg of borax, and 2.5 g of $AgNO_3$ for 250 ml of water. Coloring is developed over 10 minutes in a solution of 5 g of sodium sulfite, 1 g of hydroquinione, 0.76 g of borax for 100 ml of water. After rinsing with water, the sections are dehydrated with ethanol, thinned by xylene and lifted between blade and lamella in Canada Balsam.

The number of motor plaques was estimated by counting in each longitudinal section of the muscle.

4—Separating the Isoforms from the Acetyl-cholinesterase

A second series of control and regenerating muscles were ground at 300 rpm in a Potter glass/glass homogenizer containing 0.5 ml of extraction solution: Triton 1%, 1 M NaCl, 1 mM EGTA and 10 mM Tris/HCl pH 7 buffer. The homogenates are centrifuged for 20 minutes at 20,000 g, and 100 ml of supernatant is loaded on each density gradient.

The separation of the isoforms is performed on 5 to 20% sucrose continuous and linear gradient of containing the same concentrations of Triton, NaCl, EGTA and buffer as the homogenate. After 17 hours of centrifugation at 38,000 rpm in a 41.14 TST Kontron rotor, each gradient was divided into 40 fractions of about 0.3 ml. 1.5 ml of Ellman reagent was added to each fraction; AChE activity was measured at 412 nm, after 4 hours of incubation.

The proportion of the 16S asymmetric form was measured as a percentage of the total activity of each gradient.

5—Analysis of Choline Acetyl Transferase (CAT)

The muscles were homogenized in the Tris/HCl buffer 0.1M pH 7.6, containing 2 mM EDTA. The homogenates were centrifuged at 13,000 g for 6 minutes. The CAT activity was measured by the Rand and Johnson method (Rand J. B. and Johnson C. D., Anal. Biochem., 1981, 116, pp. 361–371).

Incubation takes place in the presence of tritiated choline (1.5 mCi), 5 mM of acetyl CoA and 200 mM of neostigmine bromide in a tricine/NaOH buffer 0.1M, pH 8 buffer. The non acetylated choline is then phosphorylated by choline kinase (5 $\mu$) in the presence of 0.1M ATP, 0.2M $MgCl_2$ for 1.25 ml of Tris buffer 0.1M, pH 8.1. The acetyl-3H synthesized choline is measured in a scintillating fluid for organic phase containing 3 mg/ml of tetraphenyl borate.

RESULTS

1—Histological and Cytochemical Study

The rapid fibers (EDL) possess a synaptic groove which is more developed than that of the slow fibers (FIGS. 7A and 7D), The subneural folds are also more developed.

Figure 7A:
FIGS. 7A to 7F represent the evidencing of the synaptic grooves of the motor plaques (P) by acetyl choline esterase (AchE). The axons (A) are revealed in brown-black by argentic impregnation on 80 mm thick longitudinal sections.
Figure 7B:

The damaged adult musclesuntreated by CMDBS, regenerate completely in about 60 days (FIG. 7B). The motor plaques, with differentiation of the synaptic groove, are clearly visible and are innervated by the axons. However, it is observed that, after 60 days of regeneration, the surface of the groove is smaller than that of the undamaged contralateral controls (FIGS. 7A and 7B).

Figure 7C:
Figure 7D:

The injection of a single dose of CMDBS (100 $\mu$l at 50 $\mu$g/ml), When the lesion is effected, considerably increases the synaptic surface. After 17 days, the treated EDL muscles show a highly differentiated and innervated groove whose surface is greater (by about 150%) than that of the undamaged controls (FIGS. 7A and 7C).

The diameters of the slow fibers (85% in the Soleus) are comparable to those of the EDL muscle but the synaptic surface is smaller (FIG. 7D) and there are fewer nerve terminals.

Figure 7E:
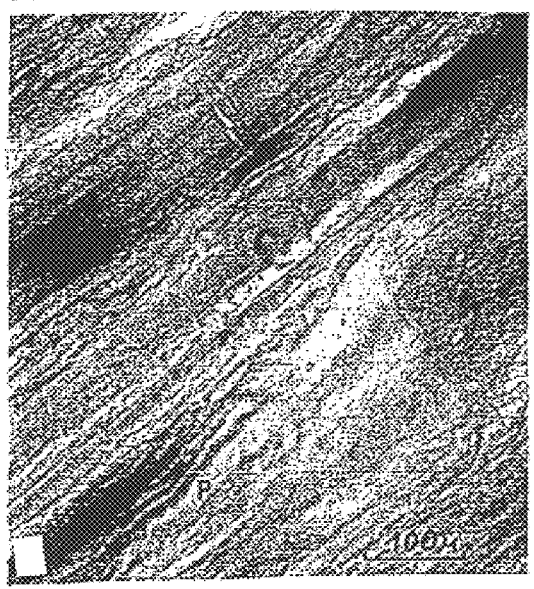

Without treatment by CMDBS, the Soleus muscle shows very incomplete regeneration. After 60 days (FIG. 7E), the plaques have a diffuse, non differentiated aspect, probably due to incomplete or absent reinnervation, and the argentic impregnation fails to show clearly the presence of axons. On the other hand, numerous anarchic axon sproutings are observed inside the muscle.

Figure 7F:
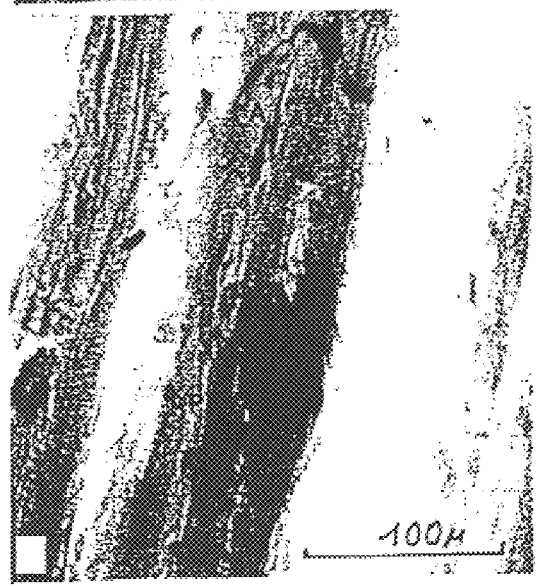

The CMDBS treatment substantially improves the reformation of the motor plaques (FIG. 7F) which present differentiated grooves comparable to those of the control muscles. The motor axons are also visible near and at the plaques level.

Figure 8:
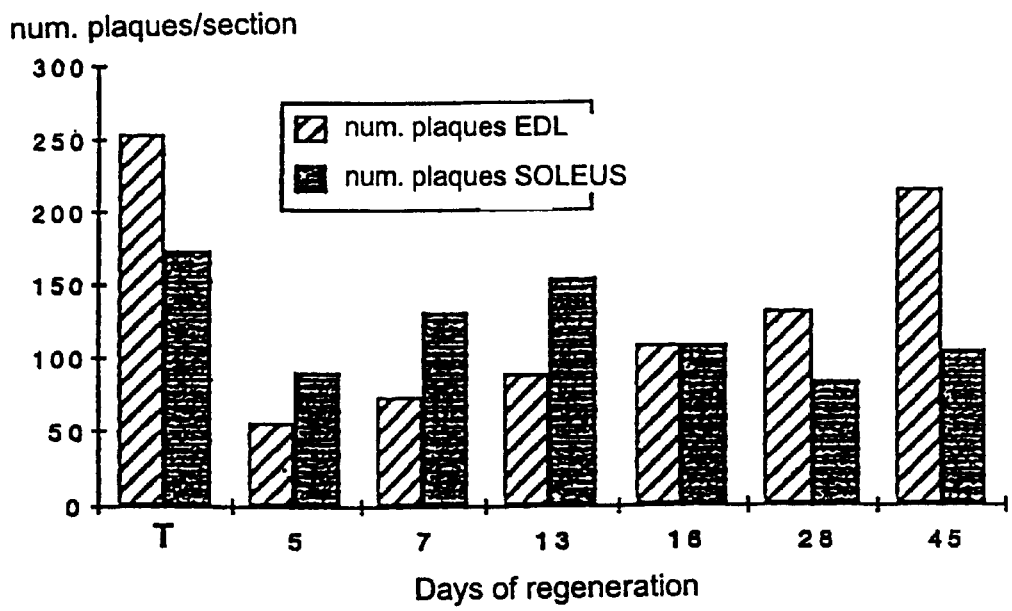
FIG. 8 illustrates the evolution of the number of motor plaques (y axis) by longitudinal section of the EDL and Soleus muscles in the course of post-trauma regeneration (x axis).

These observations were quantified by counting the plaques by longitudinal section (FIG. 8). The two muscles show very different evolutions: in the EDL muscle, 80% of the plaques disappear at the end of 3 days regeneration, after which their number increases regularly from 7 to 45 days to reach 90% of the total control. In the Soleus muscle, the initial reduction is smaller, the increase is thereafter faster but, unlike the EDL, this number drops after 13 days and stabilizes at 60% of the total control. This transitory increase of plaques between days 7 and 13 may be due to temporary synapses (ectopic synapses), the axons not returning to their former groove at the synaptic basals level.

2—Biochemical Study 2-1—Regenerated, Non Treated Muscles

The preceding observations, together with those resulting from immunocytochemistry of the lamina and the proteolytic activity, suggest that, with respect to the Soleus muscle, the matricial structures might be partially altered, especially those of the synaptic basals resulting from proteasic alterations during the initial myolysis. The acetylcholinesterase 16S (A12 asymmetric dodecamer) is focalized in the rat at the level of the synaptic basal blades (Vigny et al., mentioned above) and constitutes a very sensitive indication of the evolution of these structures.

Figure 9:
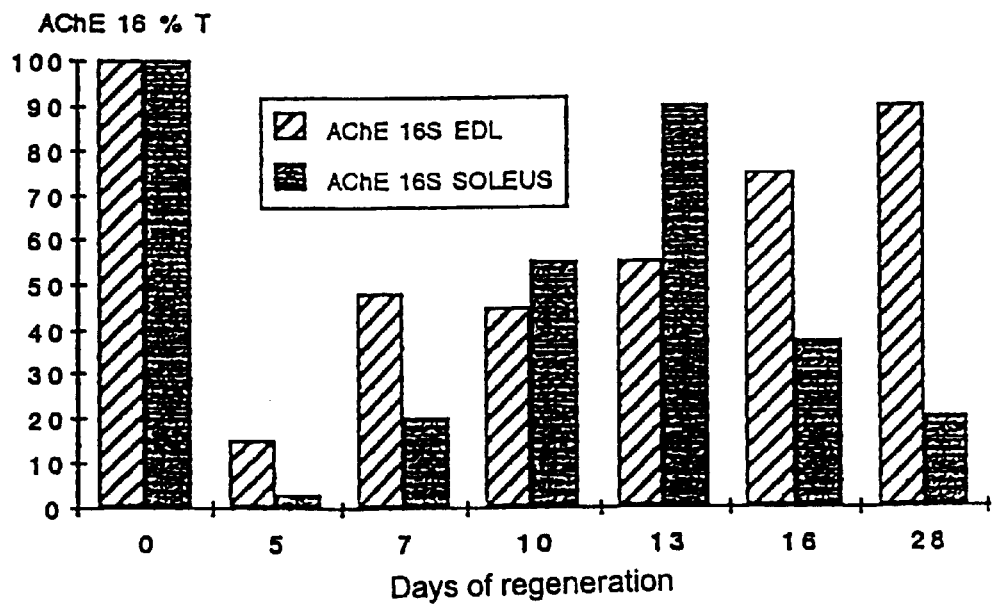
FIG. 9 illustrates the evolution of proportion (y axis) of the A12 synaptic isoform (16S) of the ACHE in the untreated EDL and Soleus muscles in the course of regeneration (x axis).

In the course of regeneration, the two muscles present different evolutions of the proportion of this isoform (FIG. 9). In the EDL muscle, after an initial fall of 85%, it increases regularly to reach 90% of the undamaged control after 28 days of regeneration.

In the Soleus muscle, the initial fall is greater (98%) followed by a rapid rise up to the 13th day, but then a sharp decrease occurs and only 20% of the control is reached after 28 days. These two results confirm the histological observations concerning the evolution of the number of plaques (FIG. 8).

2-2—Muscles Regenerated After Treatment by CMDBS

Figure 10:
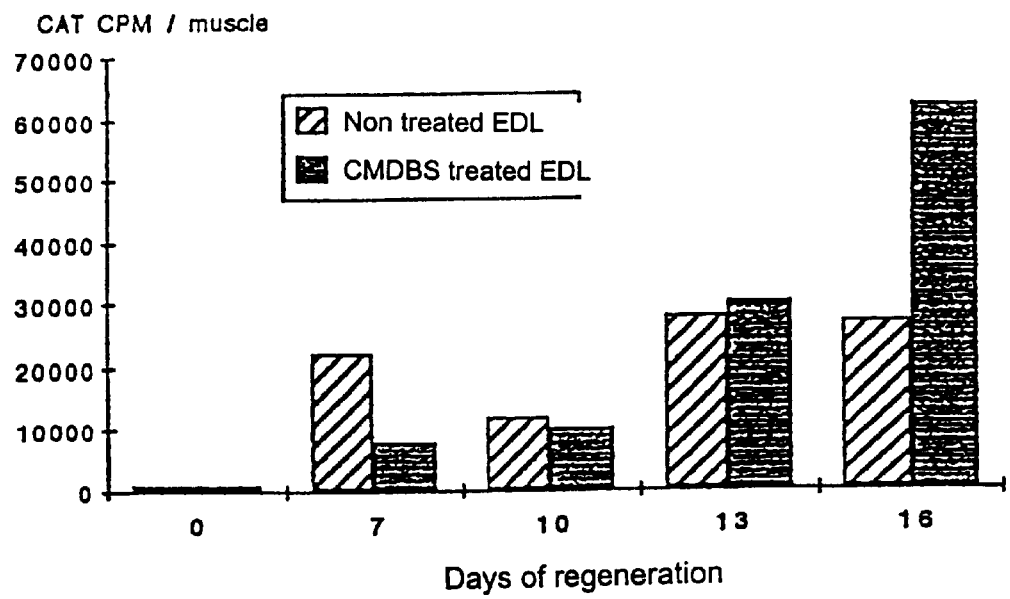
FIG. 10 illustrates the activity of the choline acetyl transferase (CAT) (y axis) of the adult rat EDL muscle in the course of regeneration (x axis).
Figure 11:
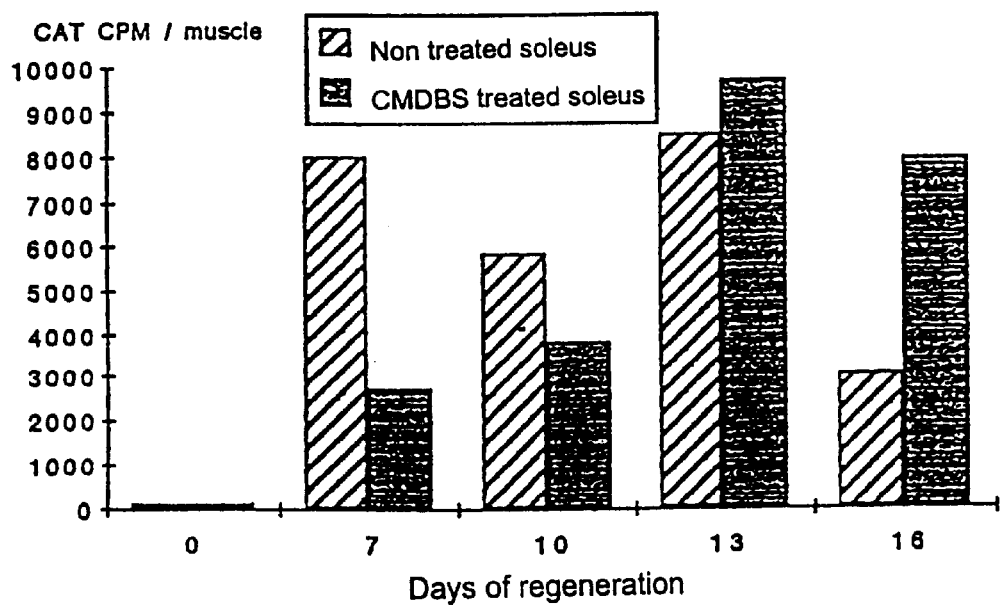
FIG. 11 illustrates the activity of the choline acetyl transferase (CAT) (y axis) of the adult rat soleus muscle in the course of regeneration (x axis).

Axonal growth inside the muscle and reinnervation were monitored by measuring the choline acetyl-transferase (CAT) activity (FIGS. 10 and 11).

A comparison of the CAT activity in these two muscles after 7 days of regeneration shows that the CMDBS reduces this activity compared to the equivalent untreated muscle. This effect is particularly marked in the case of the Soleus muscle. At this stage an axonal sprouting in the histological sections is frequently observed. At 13 days, the CAT values in the EDL muscles are comparable, whether or not the muscles have been treated, but at 16 days CAT activity is twice as high in the treated EDL muscle. This is consistent with the histological observations which showed an increase of the synaptic surface after treatment.

Where the Soleus muscle is concerned, the evolution after 13 days is different: the treated muscle does not suffer from the secondary fall of activity which occurs in the absence of CMDBS (FIG. 11).

In conclusion, the coherence of both histological and biochemical results reveals that CMDBS acts very effectively on the axonal and synaptic regeneration of the striated muscle. This effect, which is particularly pronounced in the postural slow muscle, is obtained after a single injection immediately after the lesion. This single treatment is sufficient to influence the entire subsequent regeneration.

EXAMPLE 5

Nerve Repair Activity of HBGFPP Lactic Polyacid Polymer Compounds

A. Materials and Methods

A.1 Polymer Synthesis

Synthesis of a copolymer of lactic acid modified to become an HGBFPP (fulfilling the criteria of FGF, TGFbeta, protection, elastase and plamin inhibition and low anticoagulant activity.

a) Polymer synthesis performed by co-polymerisation of different monomers substituted in a defined pre-established order.

The polymeric material can be described by the following formula (I) hereunder:

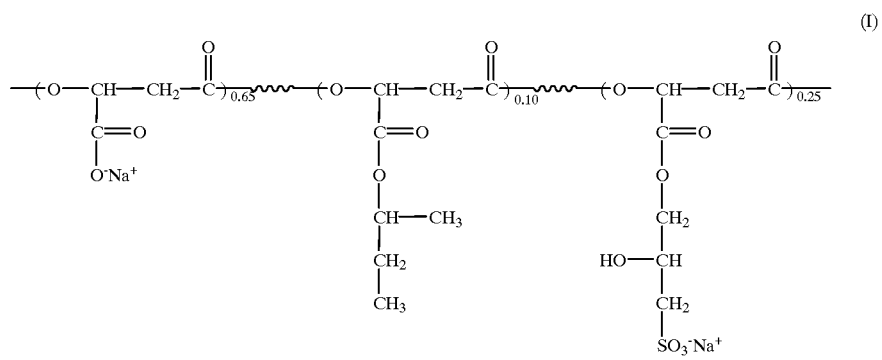

a. 1 Synthesis of Monomers from Aspartic Acid.

As a first step, bromosuccinic acid is synthesized from DL aspartic acid and sodium bromide in 2N sulfuric acid at 4° C. From this step different monoesters are synthesized. Benzyl bromosuccinate is obtained by reacting in presence of benzyl alcohol, Allyl bromosuccinate by reaction with allylic acohol. Bromosuccinate of 3 Methyl-3-buten in presence of 3-methyl-3-buten-1-ol. These monoesters are transformed in lactones by incubation in 50% Ether/Water solution at pH 7.2. After three hours, 1 volume of Dichloromethane is added and after another 3 hours incubation at 40° C., the organic phase is washed with water, then with NaCL saturated water. Lactone are then purified on silicium column and cristallized under vacuum. Allyl malolactonate and malolactonate 3-methyl-3-butene are obtained under the same conditions but at pH 7.8 a.2. Polymer Synthesis

Polymers synthesis is performed by co-polymerisation of allyl malactonate,3-méthyl-3-butène malolactonate and of butyl malolactonate in presence of tetraethylammonium benzoate under inert atmosphere during 15 days at 37° C. Basically the protocols for the copolymerisation are similar to those described by Guerin et al in MaKromol. Chem., Macromol. Symp. Vol 6, Pages 305–314, (1986). The polymer is dissolved in chloroform and the reaction is stopped by precipitation in ethanol. The polymer is then dried.

Polymers are then epoxyded in the presence of metachloroperbenzoic acid and re-precipitated in ethanol before being dried again. After a further step of hydrogen lysis, the polymers are sulfated par addition of Sodium disulfide. These steps allowed the synthesis of various polymers with defined carboxylic groups and sulfonates. The tested polymers are the following:

Copolymers noted PS containing only carboxyl groups (100%), molecular weight 10KD. Anticoagulant activity was <1.

P1S contained 60% of carboxyl groups, 10% hydrophobic groups, 10% epoxy groups and 10% S groups. Anticoagulant activity was 3.

P2S contained 75% carboxyl groups, 12% hydrophobic groups, 2% epoxy groups and 11% S groups. Anticoagulant activity was 3.

B. Results

B.1 In vitro activities of the HBGFPP polymer compounds

The polymers of formula (I) described above were tested for their ability to fulfill the criteria for HBGFPP as disclosed in the specification.

The results of the ability of the different polymers to protect FGF and TGF from proteolysis degradation and to inhibit elastase and plasmin, respectively are detailed in Table 7 hereunder. The protocols used are those already described in example 1 (FGF and TGF protection) and in example 3 (protease inhibition).

TABLE 7

| Polymers (10 µg/ml) | Protection from trypsic degradation (% FGF or TGF activity) | | protease inhibition IC50 µg/ml | |
|---|---|---|---|---|
| | FGF (criteria1) | TGF (criteria2) | Elastase (criteria3) | Plasmin (criteria4) |
| PS | 40 | 40 | 100 | 50 |
| P1S | 100 | 80 | 2 | 0.1 |
| P2S | 65 | 50 | 5 | 0.1 |

B.2 In Vivo Activities of the HBGFPP Polymer Compounds on the Reinnervation of the Skeletal Muscle of the Adult Rat in the Course of Post-traumatic Regeneration.

The protocol used is identical to the protocol described in example 4. Briefly, 10 µl of saline or of a saline solution at the concentration of 1 mg/ml of the P1S polymer was injected in 20 seconds in the muscle, using a Hamilton microsyringe fitted with a needle 50 mm in length and 0.3 mm in diameter.

The results are reported in FIG. 12.

Figure 12A:
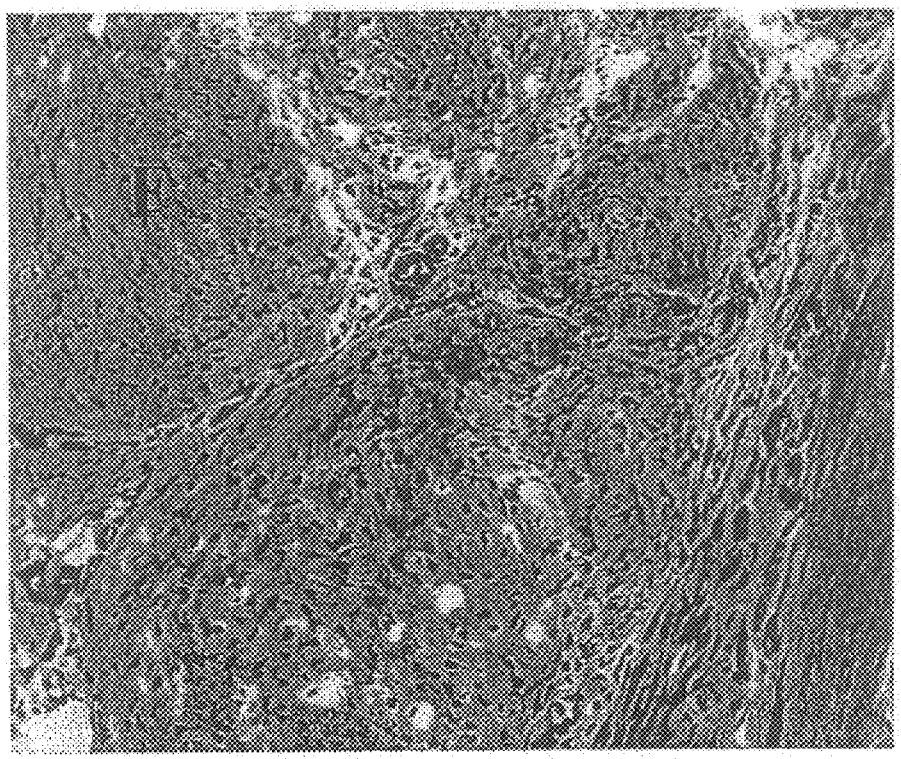
FIG. 12 is a photograph illustrating a soleus muscle section after four weeks of treatment with either (a) saline solution or (b) P1S polymer.

A tissue section of the soleus muscle after conventional Giemsa staining four weeks after treatment with saline is illustrated in FIG. 12a). The Soleus muscle, once denervated and crushed, does not regenerate and the neuromuscular junction is not reformed. Instead a degenerative process occurs, motor plates disappear, muscle fibers disappear and are replace by a fibrotic tissue. The fibrotic tissue is notably clearly visible under "F" in the photograph.

Figure 12B:
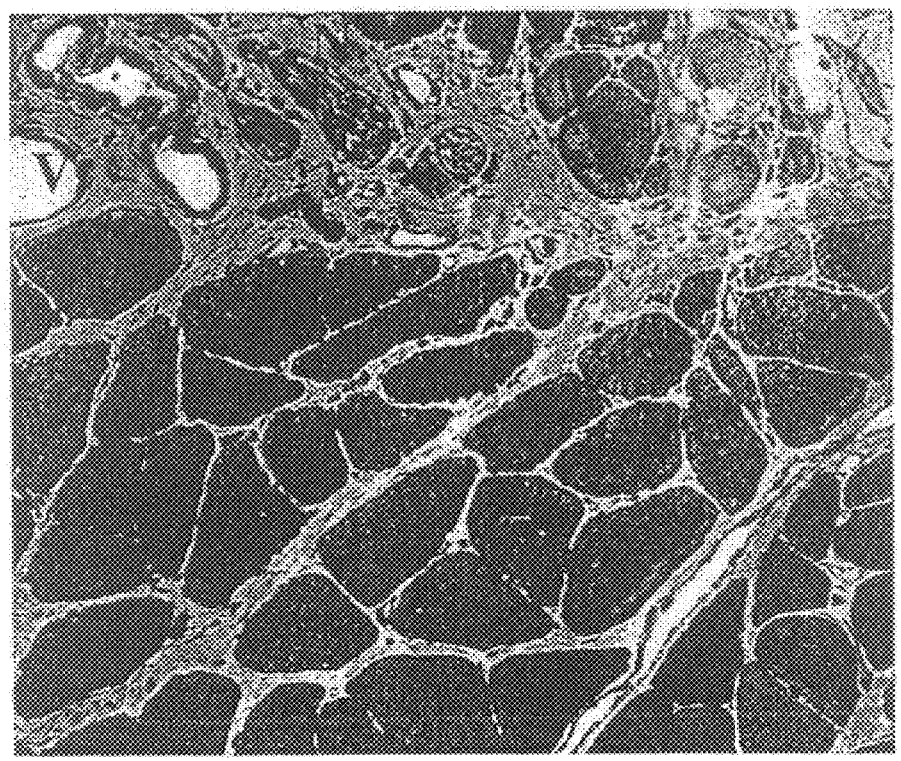

A tissue section of the soleus muscle four weeks after treatment with a saline solution of the P1S HBGFPP polymer is illustrated in FIG. 12b). The regeneration of the muscle is clearly visible and is associated with the formation of nerve connection. The vessels ("V" on the photograph) and the reinnervated myotubes ("M" on the photograph) are again observed, in contrast to the results obtained with control saline which is illustrated in FIG. 12a).

At 65 days, the results showed 85% recovery versus less then 5% in absence of HBGFPP treatment. (100% value is defined as that observed for the untouched controlateral Sol muscle).

TABLE 1

Protective effects of CMDBS and heparin against TGF degradation by trypsin

| incubation mixture at 37° C. for 10 min and containing, per milliliter, according to the indication: CMDBS or heparin (5000 μg): βTGF (50 ng): trypsin (500 μg) | % inhibiting activity of the incorporation of tritiated thymidine in CCL64 cells (after 50 times dilution of the incubation mixture) |
|---|---|
| Incubation buffer only | 0 |
| CMDBS (5000 μg) | 0 |
| Heparin (5000 μg) | 0 |
| Trypsin (1000 μg) | 0 |
| Beta TGF (50 ng) | 100 |
| Beta TGF + CMDBS (batch AM26) | 100 |
| Beta TGF + heparin | 100 |
| Beta TGF + trypsin | 5 |
| Beta TGF + CMDBS + trypsin | 75 |
| Beta TGF + heparin + trypsin | 10 |

TABLE 2

Non inhibiting effect of CMDBS with regard to trypsin

| Trypsin (10 ug/ml) + S87 | 100 |
|---|---|
| Trypsin + S87 + 5 ug/ml CMDBS | 100 |
| Trypsin + S87 + 50 ug/ml CMDBS | 100 |
| Trypsin + S87 + 500 ug/ml CMDBS | 100 |
| Trypsin + S87 + STBI | 0 |

TABLE 3

Origin, anticoagulant activity and partial composition of mesoglycan and sulodexide (supplier's information)

| | Sulodexide | Mesoglycan |
|---|---|---|
| Origin | pig duodenum | Aorta |
| Anticoagulant activity | 50–70 IU/mg | <50 IU/mg |
| Chemical composition | | |
| Dermatan sulfate | 20–35% | 25–60% |
| Chondroitine sulfate | 2–7% | 3–15% |
| Heparan sulfate | + | + |

TABLE 4

Protection of the beta TGF by various polymers

| Beta TGF | 100% |
|---|---|
| Beta TGF + trypsin | 0% |
| Beta TGF + mesoglycan | 100% |
| Beta TGF + mesoglycan + trypsin | 50% |
| Beta TGF + HSM | 100% |
| Beta TGF + HSM + trypsin | 75% |

TABLE 4-continued

Protection of the beta TGF by various polymers

| Beta TGF + sulodexide | 100% |
|---|---|
| Beta TGF + sulodexide + trypsin | 20% |
| Beta TGF + HSS | 100% |
| Beta TGF + HSS + trypsin | 45% |
| Beta TGF + dextran | 100% |
| Beta TGF + dextran + trypsin | 0% |
| Beta TGF + dextran sulfate | 100% |
| Beta TGF + dextran sulfate + trypsin | 0% |
| Beta TGF + sucrase | 100% |
| Beta TGF + sucrase + trypsin | 0% |

HSM = Heparan sulfates purified from mesoglycan
HSS = Heparan sulfates purified from sulodexide

TABLE 5

Protection of the TGF by various polymers

| | PROTECTION (in %) |
|---|---|
| FGF alone | 100% |
| FGF + trypsin | 0% |
| FGF + trypsin + heparin | 100% |
| FGF + trypsin + mesoglycan | 75% |
| FGF + trypsin + sulodexide | 70% |
| FGF + trypsin + heparinase treated mesoglycan | 0% |
| FGF + trypsin + heparinase treated sulodexide | 0% |
| FGF + trypsin + heparinase treated heparin | 0% |
| FGF + HSM + trypsin | 95% |
| FGF + HSS + trypsin | 90% |

TABLE 6

Inhibition of elastase and plasmin activities

| Compounds tested | Leukocytic elastase $IC_{50}$ in μg/ml | plasmin $IC_{50}$ in μg/ml |
|---|---|---|
| CMDBS, batch AM6 | 2.2 | 1.5 |
| T40 | >100 | >100 |
| CMDBS, batch EM5 | 10 | 7 |
| T10 CMD2B | 50 | 53 |
| T10 5CMD1B | >100 | >100 |
| T10 3CMD | >100 | >100 |
| T10 | >100 | >100 |
| Mesoglycan | 72 | 65 |
| HS mesoglycan | 20 | 22 |
| Sulodexide | 79 | 75 |
| HS sulodexide | 25 | 20 |
| Heparin | 1.8 | |
| Lipo-heparin | | 0.5 |

HSM = Heparan sulfates purified from mesoglycan
HSS = Heparan sulfates purified from sulodexide

What is claimed is:

1. A method of treating an amenable lesion of the nervous system, which comprises administering, to a subject in need of such treatment, an effective amount of an active ingredient which consists of a polymer or biopolymer, called heparin binding growth factor protector and promoter (HBGFPP), specially protecting the growth factors of families of FGFs and beta TGFs from tryptic degradation and having an anticoagulant activity of less than 50 International units per mg of polymer, wherein said polymer consists of a polymer obtained from a dextran which has been chemically modified, and wherein said polymer is associated with at least one pharmacologically acceptable excipient.

2. A method according to claim 1, wherein said polymer or biopolymer is a dextran substituted by carboxymethyl, benzylamine and sulfonate(CMDBS).

3. A method of treating an amenable lesion of the nervous system, which comprises administering an effective amount of a composition to a subject in need of such treatment, wherein the composition contains, as sole active component for treating an amenable lesion of the nervous systems, an effective amount of at least one polymer or biopolymer called heparin binding growth factor protector and promoter (HBGFPP), specifically protecting the growth factors of families of FGFs and beta TGFs from tryptic degradation and having an anticoagulant activity of less than 50 International units per mg of polymer, and wherein said polymer consists of a polymer obtained from dextran which has been chemically modified, in combination with at least one pharmacologically acceptable excipient.

4. A method according to claim 3, wherein said polymer or biopolymer is a dextran substituted by carboxymethyl, benzylamine and sulfonate (CMDBS).

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthesized

<400> SEQUENCE: 1

Ala Ala Pro Val
1
```